US010946401B2

(12) United States Patent
Baumann

(10) Patent No.: US 10,946,401 B2
(45) Date of Patent: Mar. 16, 2021

(54) LIQUID DISPENSER WITH A DISCHARGE HEAD

(71) Applicant: APTAR RADOLFZELL GMBH, Radolfzell (DE)

(72) Inventor: Tobias Baumann, Constance (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 49 days.

(21) Appl. No.: 16/314,078

(22) PCT Filed: Jul. 10, 2017

(86) PCT No.: PCT/EP2017/067300
§ 371 (c)(1),
(2) Date: Dec. 28, 2018

(87) PCT Pub. No.: WO2018/015201
PCT Pub. Date: Jan. 25, 2018

(65) Prior Publication Data
US 2019/0160481 A1 May 30, 2019

(30) Foreign Application Priority Data
Jul. 20, 2016 (EP) .................................... 16180422

(51) Int. Cl.
*B05B 11/00* (2006.01)
*B05B 1/12* (2006.01)
(Continued)

(52) U.S. Cl.
CPC ............ *B05B 11/0086* (2013.01); *B05B 1/12* (2013.01); *B05B 1/1627* (2013.01);
(Continued)

(58) Field of Classification Search
CPC ........ B05B 1/12; B05B 1/1627; B05B 1/3436; B05B 1/3452; B05B 1/3457;
(Continued)

(56) References Cited

U.S. PATENT DOCUMENTS 3,061,203 A * 10/1962 Kitabayashi ........... B65D 83/34
239/337
3,648,932 A * 3/1972 Ewald .................... B05B 7/0425
239/337
(Continued)

FOREIGN PATENT DOCUMENTS

CN 1656878 A 8/2005
EP 0 245 822 A2 11/1987
(Continued)

OTHER PUBLICATIONS

International Search Report with English translation issued in International Application No. PCT/EP2017/067300 dated Sep. 15, 2017 (7 pages).
(Continued)

*Primary Examiner* — Alex M Valvis
(74) *Attorney, Agent, or Firm* — Flynn Thiel, P.C.

(57) ABSTRACT

A discharge head for discharging liquid as an atomized spray jet and as a non-atomized liquid stream or as individual droplets. The discharge head fastening fastens to a base unit and has a liquid outlet through which liquid is discharged from a reservoir into the atmosphere, and a liquid inlet through which liquid is conducted out of the reservoir to the liquid outlet. An internal part is arranged inside an outlet channel, and a spray opening is provided on the internal part. The internal part and the outlet channel are relatively displaceable so that in a first position a bypass duct is produced between an internal wall of the outlet channel and an outer face of the internal part, the flow resistance thereof being lower than the spray duct, and in a second position is
(Continued)

partially closed wherein the flow resistance of the bypass duct is greater than the spray duct.

19 Claims, 5 Drawing Sheets

(51) Int. Cl.
*B05B 1/34* (2006.01)
*B05B 1/16* (2006.01)
*A45D 34/00* (2006.01)
*A61M 11/00* (2006.01)

(52) U.S. Cl.
CPC .......... *B05B 1/3452* (2013.01); *B05B 1/3468* (2013.01); *B05B 11/3053* (2013.01); *A45D 34/00* (2013.01); *A61M 11/006* (2014.02); *B05B 11/3001* (2013.01)

(58) Field of Classification Search
CPC ............... B05B 1/3478; B05B 11/0086; B05B 11/3001; B05B 11/3053; B65D 83/44; B65D 83/7532; A45D 34/00
USPC ................. 239/436–441, 396; 222/231, 372, 222/379–382, 402.17
See application file for complete search history.

(56) References Cited

U.S. PATENT DOCUMENTS

| | | | | |
|---|---|---|---|---|
| 3,994,442 | A | * | 11/1976 | Hoening ............... B05B 1/3436 239/472 |
| 4,358,057 | A | * | 11/1982 | Burke ...................... B05B 1/12 222/380 |
| 4,911,361 | A | | 3/1990 | Tada |
| 5,261,574 | A | | 11/1993 | Jouillat et al. |
| 5,590,837 | A | * | 1/1997 | Grogan ................. B05B 1/3478 239/478 |
| 9,527,635 | B2 | | 12/2016 | Metz |
| 9,957,100 | B2 | | 5/2018 | Jasper et al. |
| 2005/0178858 | A1 | | 8/2005 | Roman |
| 2016/0023221 | A1 | | 1/2016 | Metz |

FOREIGN PATENT DOCUMENTS

| | | |
|---|---|---|
| EP | 0 638 366 B1 | 2/1995 |
| EP | 0 729 792 A2 | 9/1996 |
| WO | WO 2014/138421 A1 | 9/2014 |
| WO | WO 2015/106776 A1 | 7/2015 |

OTHER PUBLICATIONS

Written Opinion of International Searching Authority issued in International Application No. PCT/EP2017/067300 dated Sep. 15, 2017 (5 pages).
Chinese Office Action with English Translation issued in corresponding Chinese Application No. 201780044945.5 dated Jun. 3, 2020 (12 pages).

* cited by examiner

LIQUID DISPENSER WITH A DISCHARGE HEAD

FIELD OF APPLICATION AND PRIOR ART

The invention relates to a liquid dispenser, as claimed in the preamble of claim 1, which is configured for selectively discharging liquid, on the one hand, in the form of an atomized spray jet and, on the other hand, in the form of a non-atomized liquid stream or in the form of individual droplets.

A dispenser for discharging liquids having two outlet channels which in each case have a separate outlet opening is disclosed in WO 2015/106776 A1. By a rotational movement it is possible to control into which of the outlet channels the liquid to be discharged flows.

Object and Solution

It is the object of the invention to provide a liquid dispenser which in a particularly convenient manner permits the discharge of liquid with a variable discharge characteristic.

A generic liquid dispenser has a base unit with a liquid reservoir for receiving liquid before the discharge and a discharge head attached to the base unit.

In principle, different constructions are possible for discharging the liquid.

The liquid dispenser according to a first construction may have a pump device which may be actuated by a relative translatory movement of the discharge head relative to the base unit and which conveys liquid out of the liquid reservoir into the discharge head. In a design with a pump device, therefore, depressing the discharge head relative to the base unit effects the discharge. The pump is preferably provided on the base unit and has an outlet tube, the discharge head being positioned thereon. When the discharge head is depressed a pump piston is displaced together with the outlet tube, said pump piston conveying liquid through the outlet tube into the discharge head.

The liquid reservoir in the second cited construction may be alternatively configured as a pressure accumulator, wherein in such a case the liquid dispenser also has an outlet valve which may be actuated by a relative translatory movement of the discharge head relative to the base unit and which conveys liquid out of the liquid reservoir into the discharge head. The design with a liquid reservoir in which the liquid is stored under pressure is regarded as advantageous since it permits an uninterrupted discharge over a long period of time. The displacement of the discharge head relative to the base unit in this case effects an opening of the outlet valve so that the pressurized liquid may flow out of the liquid reservoir into the discharge head.

The particularity according to the invention is in the design of the discharge head of this dispenser. This discharge head is conventionally provided for attachment onto a base unit of the liquid dispenser, which comprises the liquid reservoir. The discharge head has a housing which is configured for the stationary or linearly movable or linearly and rotatably movable fastening to the base unit of the liquid dispenser. The discharge head has a liquid outlet through which liquid may be discharged from the liquid reservoir into a surrounding atmosphere as well as a liquid inlet through which liquid may be conducted out of the liquid reservoir to the liquid outlet.

The liquid outlet has an outlet channel penetrating the outer face of the housing. An internal part is arranged inside this outlet channel, a spray opening as the end of a spray duct being provided on the front face of said internal part facing in the direction of the surrounding atmosphere. The internal part and the outlet channel are displaceable relative to one another so that in a first relative position a bypass duct is produced between an inner wall of the outlet channel and an outer face of the internal part, the flow resistance thereof being lower than that of the spray duct and in a second relative position this bypass duct is at least partially closed so that the flow resistance of the bypass duct is greater than that of the spray duct.

In the discharge head of a liquid dispenser according to the invention, therefore, two different liquid paths are provided, said liquid paths both discharging into a common liquid outlet of the discharge head. One of these liquid paths leads through the spray duct which penetrates the internal part arranged in the outlet channel. This spray duct is formed by a suitable geometric shape for producing a spray jet, for example by the provision of a swirl chamber upstream of the spray opening or by one or more correspondingly finely dimensioned spray nozzles. The second liquid path leads through the outlet channel but not through the internal part in the outlet channel. This second spray path which flows past the internal part serves for discharging the liquid with lower kinetic energy so that a continuous liquid stream or the formation of droplets is present.

The internal part which is arranged in the outlet channel and which is penetrated by the spray duct is movable relative to the outlet channel so that the ratio between the flow resistance of the first liquid path through the spray duct and the flow resistance of the second liquid path through the bypass duct may be influenced. Depending on the relative position, the flow resistance on the first or the second liquid path is lower, so that at least the majority of the liquid is discharged along this path with a lower flow resistance. If the liquid flows through the spray duct, it is discharged in the form of a spray jet at the liquid outlet. If the liquid flows through the bypass duct, it leaves the liquid outlet in the form of a continuous liquid stream with lower kinetic energy or in the form of individual droplets.

By the design of the discharge head with a single liquid outlet, a very intuitive and simple use is possible. This is further reinforced by the variations in design for the actuation, explained in more detail below.

In one development it is provided that in the first relative position the bypass duct is closed so that liquid may only enter the surrounding atmosphere through the spray duct and/or in that in the second relative position an inlet into the spray duct is closed so that liquid may only enter the surrounding atmosphere through the bypass duct.

Whilst in principle it is not necessarily required that the bypass duct and/or the flow channel is completely closed in the respective end positions, this is advantageous in order to conduct all of the liquid respectively through the channel which is not closed.

In one variant, the inner wall of the outlet channel is directly formed by surfaces of the housing and the internal part is displaceable relative to the housing.

"Housing" within the meaning of the invention is understood as all parts of the discharge head which form in a fixed manner relative to one another the main unit of the discharge head. The cited variant of the invention provides that the inner wall of the outlet channel is formed by surfaces of the housing. In this design, however, the internal part is not part of the housing but is displaceable relative to the housing in order to influence the liquid path depending on the relative position from the housing.

In a further variant, the inner wall of the outlet channel is formed by an outlet sleeve which is displaceable relative to the housing and is thus also displaceable relative to the internal part which is part of the housing.

In this alternative variant, therefore, the internal part of the housing is immovable and also immovable relative to the other housing parts, whilst the inner wall of the outlet channel is displaceable, in particular, by it being part of an outlet sleeve which may be displaced relative to the housing.

For producing the desired spray pattern in the spray duct, said spray duct preferably comprises a swirl chamber. In such a swirl chamber the liquid flows in an eccentric direction so that it introduces a swirl into the liquid inside the swirl chamber. This swirl is maintained and leads to the formation of a spray cone when the liquid is discharged.

For the structural implementation of a geometry for producing a spray jet, it is advantageous if the internal part forms an outer wall portion, a spray component being introduced therein. This spray component may, in particular, at least partially form an inner wall of the swirl chamber in which the spray jet is produced.

The bypass duct, through which the liquid flows for forming a continuous liquid stream or for droplet formation, extends between the inner wall of the outlet channel and an outer wall of the internal part. Preferably, this bypass duct is configured as an annular channel which surrounds the internal part.

The relative mobility of the internal part and the outlet channel is preferably a translatory, i.e. non-rotational, mobility. This is to be understood in that components defining a rotational axis are not provided, but rather the internal part or the outlet channel are slidable along a track, preferably in a linearly movable manner. In particular, it is advantageous if the relative mobility is aligned with the main direction of extent of the outlet channel and/or the discharge direction of the liquid.

The relative displacement of the internal part relative to the outlet channel may be implemented in different ways. One possible design provides that the internal part and the outlet channel are movable in a translatory manner via a threaded drive, so that the preferably linear relative displacement takes place by a rotational adjusting movement on the outlet channel or on the internal part.

For the purposes of relative displacement, in particular, a switching surface may be provided for manual actuation, the relative position of the outlet channel being able to be changed thereby relative to the internal part.

The switching surface may be provided directly on an outlet sleeve which is movable relative to the housing or on the internal part which is movable relative to the housing. In such a design, therefore, the switching surface is fixed to the outlet sleeve or to the internal part, so that a displacement of the outlet sleeve or of the internal part relative to the housing, associated with the action of force on the switching surface, also directly influences the relative position of the internal part to the outlet channel.

Alternatively, the switching surface may be coupled by means of a gear mechanism to the outlet channel which is movable relative to the housing or to the internal part which is movable relative to the housing. In this alternative design, a gear mechanism is provided by which it is possible, for example, to effect a directional change. Thus, for example, the movement of the switching surface, in a direction for a relative displacement of the internal part and the outlet sleeve to one another, may take place in a second direction deviating therefrom.

A restoring spring which acts between the internal part and the outlet channel may be provided, so that the internal part and the outlet channel are always acted upon by force in the direction of the first or the second relative position and are displaced counter to the force of the restoring spring by the action of force on the switching surface.

The restoring spring results in the discharge head adopting its initial position again when the switching surface is no longer acted upon by force. This may be implemented firstly by the relative arrangement of the internal part and the outlet channel being able to be blocked in the position which is effected by the action of force on the switching surface. However, a design in which the action of force on the switching surface not only effects the displacement of the internal part and the outlet channel counter to the force of the spring, but also the discharge itself, is advantageous. Thus, depressing the switching surface initially effects the displacement of the internal part and the outlet channel relative to one another, and subsequently the discharge process takes place along the liquid path which is produced by the action of force on the switching surface.

The discharge head may have a variable internal volume of liquid which is increased by pushing in the outlet sleeve. By a variable internal volume it is achieved, in particular in a design with an outlet sleeve which is displaceable relative to the housing, that the displacement of this outlet sleeve into the housing does not lead to undesired liquid discharge. By means of the variable volume, the liquid which would otherwise be forced out of the outlet sleeve is able to be received in the discharge head.

The outlet channel may have a shape tapering in the direction of the surrounding atmosphere. The outlet channel with the tapering shape is particularly suitable for producing the closable bypass duct. The internal part in this case has an outer diameter which is smaller than the maximum clear cross section of the outlet channel but larger than the minimum clear cross section. Thus a displacement of the internal part relative to the tapering portion may be used for closing the bypass duct.

The switching surface for displacing the internal part relative to the outlet channel is preferably provided on a side of the discharge head remote from the base unit. The switching surface is also preferably movable relative to the housing of the discharge head in a direction which corresponds (+/−20°) to the relative translatory direction of movement of the discharge head relative to the base unit.

Whilst in principle other designs are also possible, further liquid dispensers in which depressing the discharge head effects the discharge are regarded as advantageous. To this end, an actuating surface is provided on the upper face of the discharge head. If the switching surface is also provided there, this permits the switching surface to be operated by the same finger for influencing the discharge characteristic as for depressing the discharge head. A particular advantage results if the relative mobility of the switching surface to the housing of the discharge head substantially coincides with the relative mobility of the discharge head, since as a result it may be achieved that a single movement initially influences the flow path in the discharge head and subsequently starts the discharge process. In such a design, it may be provided that the upper face of the discharge head is divided into two. The action of force in a first part in which the switching surface is provided leads to the described alteration to the flow path and subsequently to the discharge. The action of force on the discharge head adjacent to the switching surface leads to a discharge process, without the flow path having been previously adjusted.

In one particular design, the discharge head is configured to be rotatable about a rotational axis relative to the base unit. In this case, a gear mechanism is provided, the rotational movement of the discharge head effecting thereby a relative displacement of the outlet channel relative to the internal part. The gear mechanism comprises a guide element with an angular-dependent spacing from the rotational axis and which is provided on the internal part or the outlet sleeve of the discharge head or on the base unit, and a guide slider which is in engagement with the guide element and which is provided opposite the guide element on the base unit and/or on the internal part or on the outlet sleeve of the discharge head.

The angular-dependent spacing is preferably provided in the manner of a spiral-shaped portion. If the guide slider slides along the guide element, it also changes thereby its spacing from the rotational axis, i.e. a radial displacement. Alternatively, with a radially fixed guide slider the guide element could also perform a radial displacement. This radial displacement may be used in order to displace radially the outlet sleeve or the internal part.

BRIEF DESCRIPTION OF THE DRAWINGS

Further advantages and features of the invention are disclosed in the claims and in the following description of preferred exemplary embodiments of the invention which are described hereinafter with reference to the figures.

DETAILED DESCRIPTION OF THE EXEMPLARY EMBODIMENTS

Figures 1, 2:
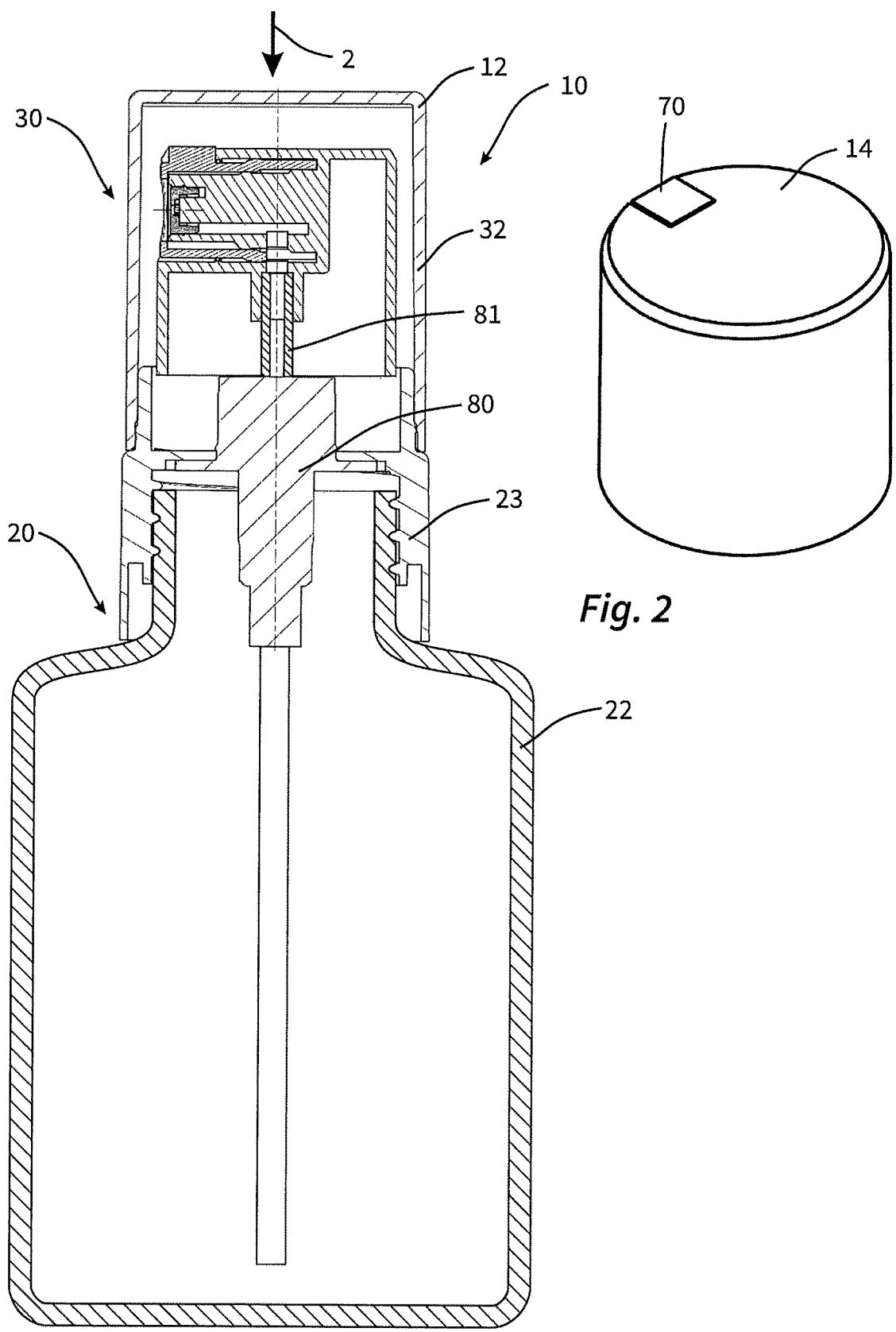
FIG. 1 shows a first exemplary embodiment of a liquid dispenser with a discharge head in a sectional view.
FIG. 2 shows the discharge head of the liquid dispenser in a perspective view, in which the upper face of the discharge head is visible.

FIG. 1 shows in an overall view a first exemplary embodiment of a liquid dispenser 10 according to the invention. This liquid dispenser 10 has a base unit 20 comprising a liquid reservoir 22 and a housing part 23 positioned thereon, which together secure a pump device 80, an outlet tube 81 being provided on the upper end thereof. A discharge head 30, which is covered by a protective cap 12 in the state of FIG. 1, is positioned thereon. This discharge head 30 may be depressed in the direction of the arrow 2 for the purpose of discharging liquid.

The discharge head 30 is provided to dispense liquid optionally in the form of a spray jet or in the form of a continuous liquid stream and/or droplets.

In order for the user to be able to influence this procedure, the discharge head is provided in the manner shown in FIG. 2 with a switching surface 70 in the region of an actuating surface 14. The relative arrangement of this switching surface 70 to the housing 32 of the discharge head 30 and the actuating surface 14 determines in which form the liquid is discharged.

The different configurations of the discharge head 30 are described with reference to FIGS. 3 and 4.

The discharge head 30 has a liquid inlet 38 which is fastened to the outlet tube 81 of the pump device 80 in the manner already described. From the liquid inlet 38 the liquid is conducted to a single liquid outlet 34 which the liquid to be discharged traverses when discharged. To this end, in the spray configuration of FIG. 3 the liquid flows along a liquid path 4 which leads through a radial inlet 53 into an internal part 50 of the discharge head 30, which is arranged fixedly relative to the housing 32 of the discharge head. The internal part is penetrated by a spray duct 54 along which the liquid path 4 extends as far as a swirl chamber 58. In this swirl chamber the liquid to be discharged is provided with a swirl so that it emerges through a spray opening 56 on the front face 52 of the internal part 50 in the form of a spray jet, without coming into contact again with other housing parts after being discharged. The path of the liquid in the spray configuration is illustrated by the liquid path 4 in FIG. 3.

The internal part 50 is arranged inside an outlet channel 36 which is displaceable in the horizontal direction relative to the housing 32 of the discharge head 30 in a translatory linear manner.

Figure 4:
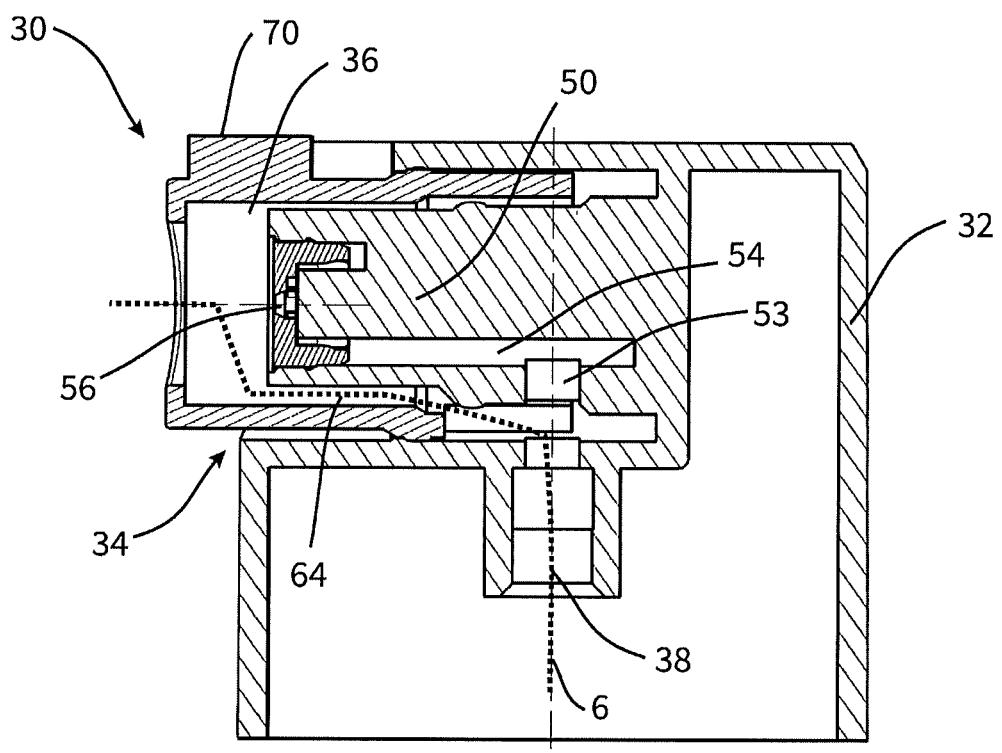

FIG. 4 shows the droplet configuration of the discharge head 30. In this droplet configuration, an outlet sleeve 60, the inner face thereof forming the outlet channel 36, is displaced such that a bypass duct 64 is opened. The flow path of the liquid is now the liquid path 6 which leads past the internal part 50 inside the outlet channel 36 as far as the liquid outlet 34.

Since the clear cross section of the bypass duct 64 is significantly larger than that of the spray opening 56, the liquid flows at a slower speed to the liquid outlet 34 and thus may be discharged in a relatively depressurized manner.

Figure 3:
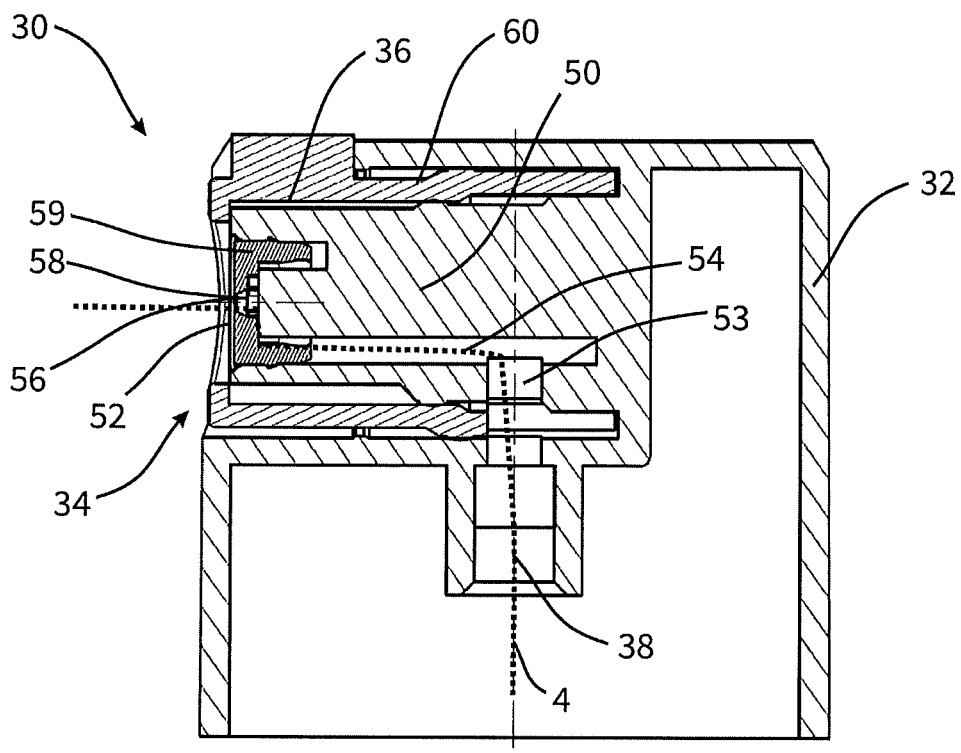
FIGS. 3 and 4 show the discharge head in sectional view in two different configurations.

In the exemplary embodiment of FIGS. 1 to 4, the bypass duct 64 is closed in the spray configuration of FIG. 3. In the droplet configuration of FIG. 4, however, the spray duct 54 is open as before. Due to the increased flow resistance of the spray duct 54 and the spray opening 56, however, the entire liquid or almost the entire liquid flows through the bypass duct 64 in the droplet configuration of FIG. 4.

In alternative designs, however, it may also be provided that the spray duct 54 is fully closed in the droplet configuration. This is structurally easy to achieve by a corresponding lengthening of the outlet sleeve 60 and the introduction of a radial through-passage, so that by means of this lengthening the lengthened outlet sleeve in the configuration of FIG. 4 closes the access to the inlet 53 of the internal part 50.

Figure 5:
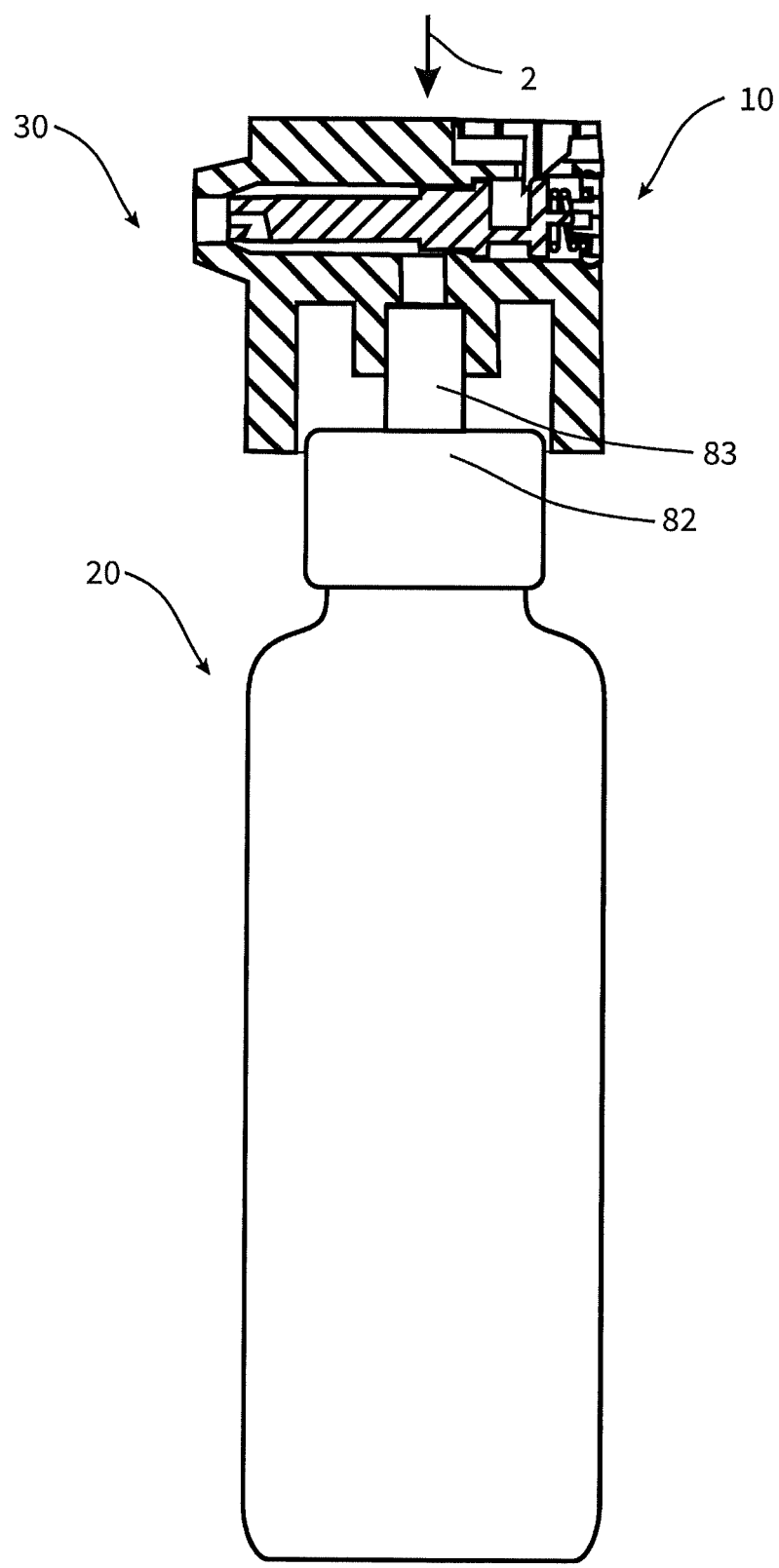
FIG. 5 shows a second exemplary embodiment of a liquid dispenser with a discharge head in a partially sectional view.

FIG. 5 shows an alternative design. In the liquid dispenser 10 shown here, a base unit 20 and a discharge head 30 which is displaceable in the direction of the arrow 2 are provided once again. In this design, however, the base unit 20 is provided with a liquid reservoir 22 which is provided as a pressure accumulator. Instead of the pump device 80, therefore, a valve device 82, not shown in more detail, is used, said valve device being able to be opened by displacing an outlet pipe 83 in the direction of the arrow 2.

In principle, however, even in this design a base unit with a pump device corresponding to the exemplary embodiment set forth above may be used. Also in the exemplary embodiment set forth above a pressure accumulator with valve device may be used instead of the liquid reservoir with pump device.

Figure 6:
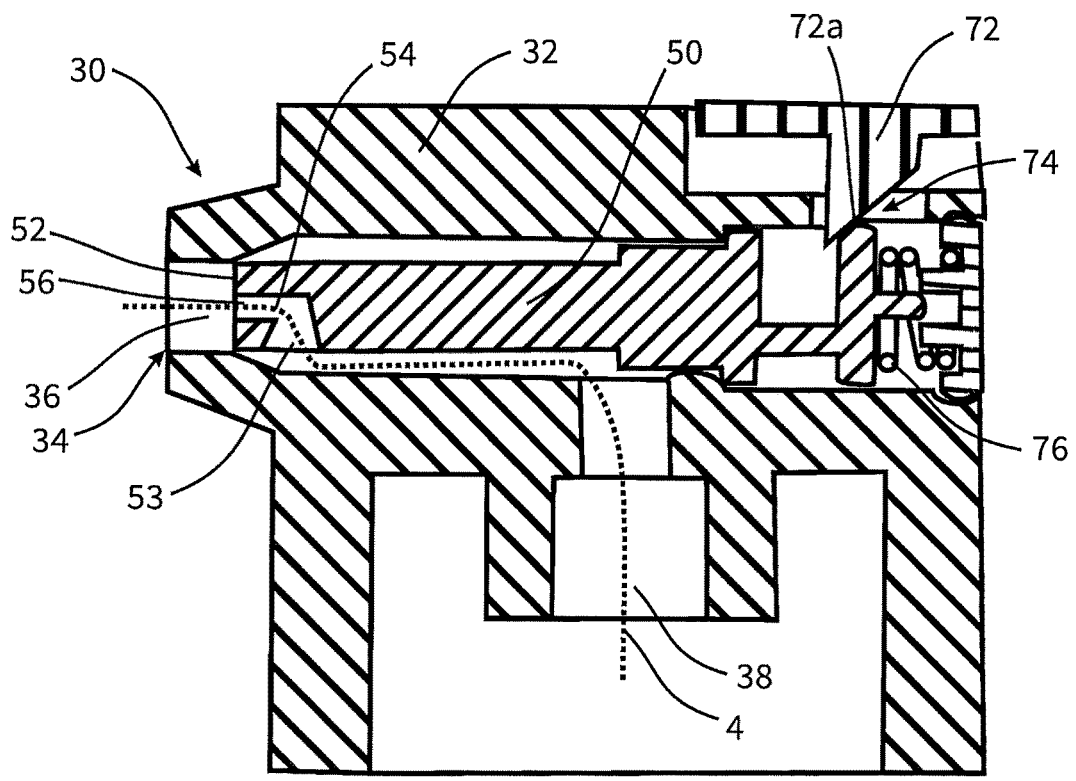
FIGS. 6 and 7 show the discharge head in sectional view in two different configurations.
Figure 7:
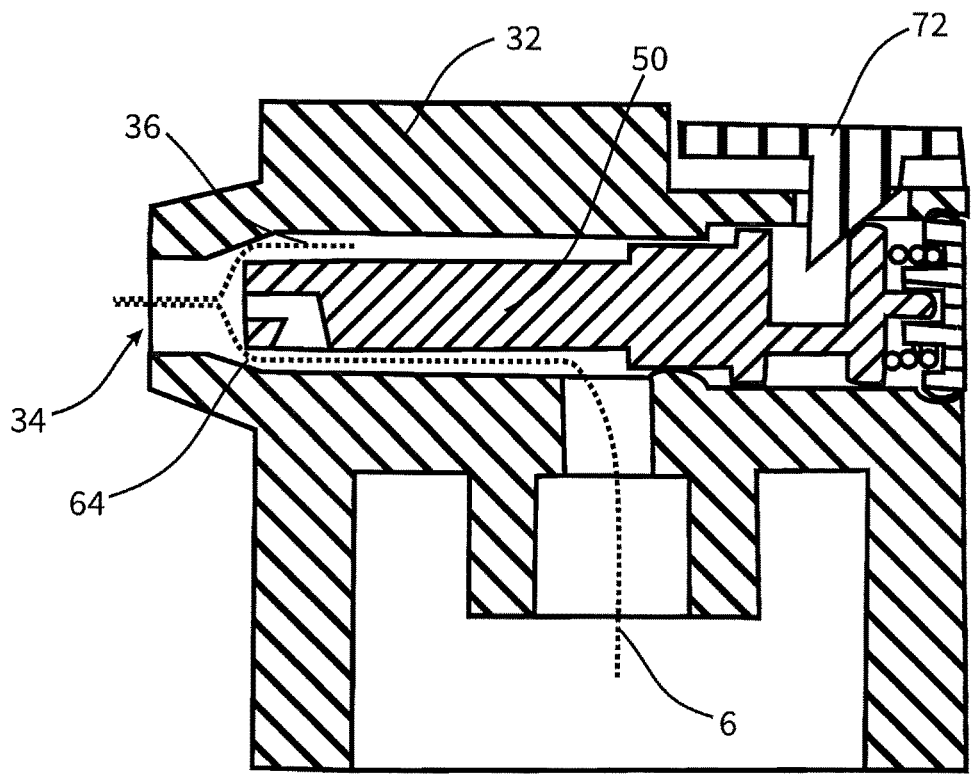

With reference to FIGS. 6 and 7, the two configurations of the discharge head 30 are described.

In the configuration of FIG. 6, the discharge head is configured for producing a spray jet. The liquid flowing through the liquid inlet 38 enters the inlet 53 of the spray duct 54 since no other path leads to the liquid outlet 34. The liquid is dispensed through the relatively narrow spray opening 56 at the end of the spray duct 54. A swirl chamber could also be used here corresponding to the first exemplary embodiment, although a geometric design specifically adapted thereto is not shown in the figures. Also possible is a design with one or more fine nozzle openings for producing a spray jet.

In the configuration of FIG. 7, the internal part 50 is displaced to the right relative to the housing 32, with reference to the drawings. As a result, the bypass duct 64 is opened so that now the liquid may flow in turn in a relatively depressurized manner to the liquid outlet 34. Thus with regard to the internal part 50 and the outlet channel 36, the design relative to the first exemplary embodiment is reversed. In this design of FIGS. 5 to 7, the internal part 50 is displaceable in a linear manner relative to the housing 32, whilst the outlet channel 36 remains fixed in position relative to the housing 32.

The particularity of this exemplary embodiment, however, is in particular in the manner of the actuation. A switching surface 72 which may also be depressed in the direction of the arrow 2 is provided on the upper face of the discharge head 30. This switching surface is coupled to a rear end of the internal part 50 via an oblique plane 72a. Additionally, the internal part 50 is acted upon by force by means of a restoring spring 76 in the direction of the spray configuration of FIG. 6.

If in the manner illustrated in FIG. 7 the switching surface 72 is now depressed relative to the housing 32, with a simultaneous compression of the restoring spring 76 which is configured as a compression spring, the internal part 50 is displaced to the right and thus the bypass duct 64 is opened.

Thus, depending on the actual location of the action of force on the discharge head, it is possible to select one of two configurations. If the discharge head is depressed in the region of the switching surface 72, this leads to the discharge of a substantially depressurized liquid stream. If the actuation takes place remotely from the switching surface 72, the spray configuration of FIG. 6 is produced, so that the liquid is discharged in the form of a spray jet.

Figure 8:
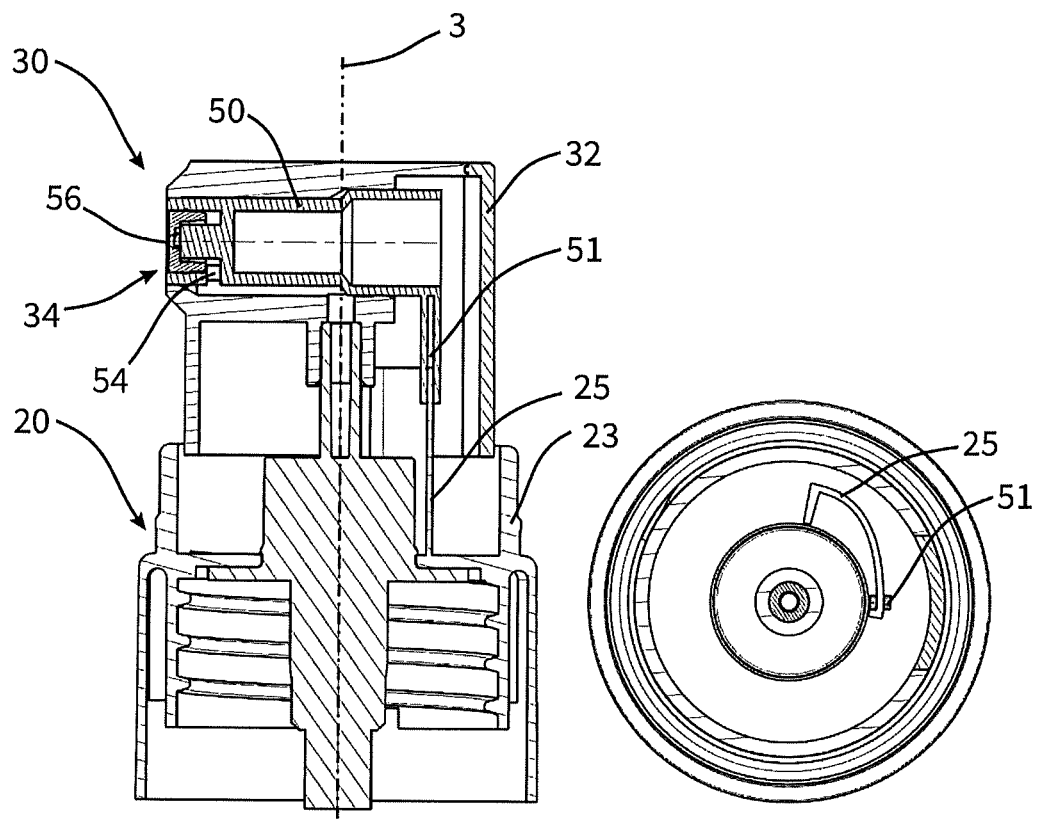
FIGS. 8 and 9 show a second exemplary embodiment of a liquid dispenser with a discharge head in a partially sectional view in two different configurations.
Figure 9:
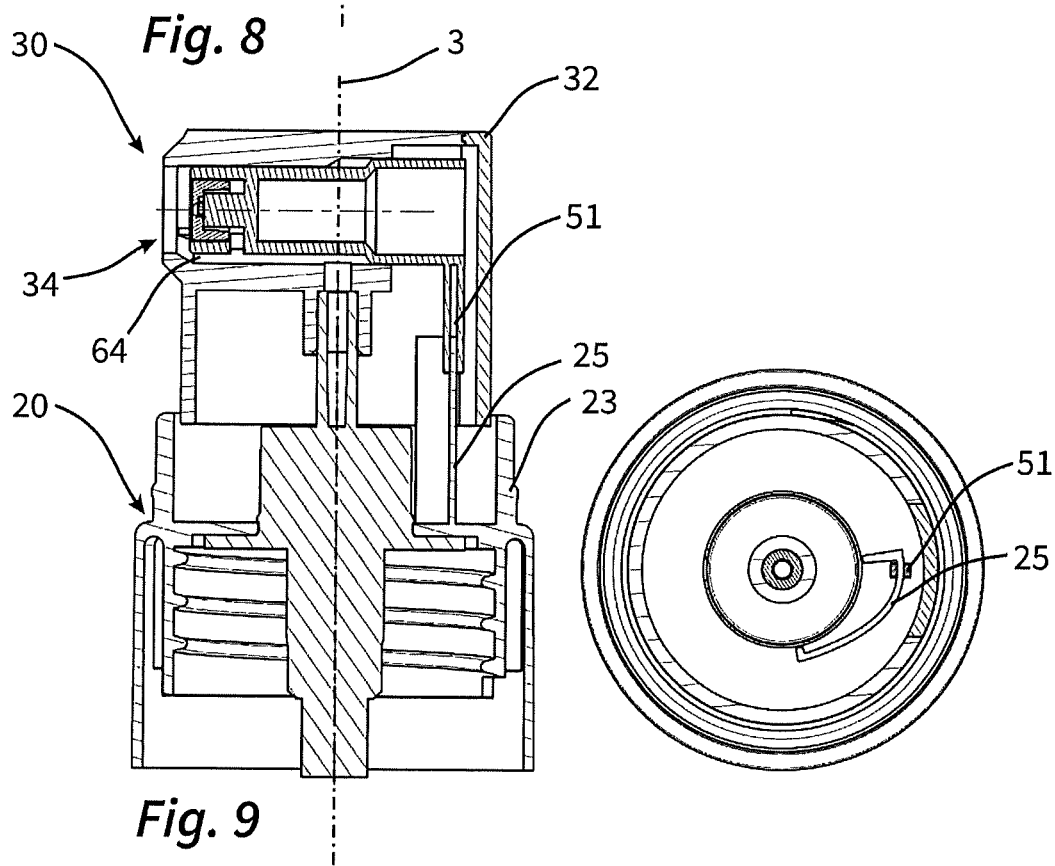

FIGS. 8 and 9 show a third exemplary embodiment in which the internal part 50 is displaceable relative to the housing 32, coinciding with the design of FIGS. 5 to 7, and in which a swirl chamber is provided for producing a spray jet, coinciding with the exemplary embodiment of FIGS. 1 to 4.

However, it is a design in which a switching surface is not provided. Instead, located on the base unit 20 is a housing part 23 which is connected fixedly in terms of rotation thereto, with a projection protruding into the discharge head, said projection acting as a guide element 25 and being at a variable spacing from the outlet pipe 83 in the manner of a spiral-shaped portion. Corresponding to this guide element 25, a projection is provided on the internal part 50 which is linearly movable relative to the housing 32, said projection having a deep groove which serves as guide slider 51 and into which the guide element 25 engages on the base part side. The action thereof is such that by a rotational movement of the discharge head 30 about a rotational axis 3 the position of the internal part 50 may be influenced, and thus the two described configurations, the spray configuration, on the one hand, and the droplet configuration, on the other hand, may be produced. Due to the depth of the groove in the guide slider 51, it is nevertheless ensured that the projections do not hinder the depression of the discharge head.

The invention claimed is:

1. A liquid dispenser comprising:
   a base unit with a liquid reservoir for receiving liquid before a discharge thereof;
   a discharge head for fastening to the base unit of the liquid dispenser; and
   a pump device that is configured to be actuated by a relative translatory movement of the discharge head relative to the base unit and that conveys liquid out of the liquid reservoir into the discharge head or the liquid reservoir is configured as a pressure accumulator and the liquid dispenser has a valve device configured to be actuated by a relative translatory movement of the discharge head relative to the base unit and conveys liquid out of the liquid reservoir into the discharge head;
   the discharge head comprising a housing which is configured for stationary or linearly movable or linearly and rotatably movable fastening to the base unit of the liquid dispenser;
   the discharge head having a liquid outlet through which liquid is configured to be discharged from the liquid reservoir out of the discharge head;
   the discharge head having a liquid inlet through which liquid is conducted out of the liquid reservoir to the liquid outlet;
   the discharge head being configured for selectively discharging liquid either in the form of an atomized spray jet and in the form of a non-atomized liquid stream or individual droplets;
   the liquid outlet having an outlet channel penetrating the housing;
   an internal part being arranged inside the outlet channel, a spray opening at an end of a spray duct being provided on a front face of said internal part facing outward; and
   the internal part and the outlet channel being displaceable relative to one another so that in a first relative position a bypass duct is produced between an inner wall of the outlet channel and an outer face of the internal part, whereby the bypass duct has a flow resistance being lower than that of the spray duct, and the bypass duct bypasses the spray duct and the spray opening, and in a second relative position this bypass duct is at least partially closed by the inner wall of the outlet channel so that the flow resistance of the bypass duct is greater than that of the spray duct.

2. The liquid dispenser as claimed in claim 1, wherein:
   in the first relative position, the bypass duct is closed so that liquid may only be dispensed through the spray duct, and/or
   in the second relative position, an inlet into the spray duct is closed so that liquid may only be dispensed through the bypass duct.

3. The liquid dispenser as claimed in claim 1, wherein:
   the inner wall of the outlet channel is directly formed by surfaces of the housing and the internal part is displaceable relative to the housing, or
   the inner wall of the outlet channel is formed by an outlet sleeve which is displaceable relative to the housing and is thus also displaceable relative to the internal part which is part of the housing.

4. The liquid dispenser as claimed in claim 1, wherein:
   the spray duct comprises a swirl chamber, liquid flowing therein in a direction deviating from a radial direction.

5. The liquid dispenser as claimed in claim 1, wherein:
the internal part and the outlet channel are linearly movable in a translatory manner relative to one another.

6. The liquid dispenser as claimed in claim 1, comprising:
a switching surface provided for manual actuation, a relative position of the outlet channel being able to be changed thereby relative to the internal part;
wherein the switching surface is provided directly on an outlet sleeve which is movable relative to the housing or on the internal part which is movable relative to the housing.

7. The liquid dispenser as claimed in claim 1, comprising:
a switching surface provided for manual actuation, a relative position of the outlet channel being able to be changed thereby relative to the internal part;
wherein the switching surface is coupled by a mechanism to the outlet channel which is movable relative to the housing or to the internal part which is movable relative to the housing.

8. The liquid dispenser as claimed in claim 7, further comprising:
a restoring spring which acts between the internal part and the outlet channel, so that the internal part and the outlet channel are always acted upon by force in a direction of the first or the second relative position and are displaced counter to the force of the restoring spring by an action of force on the switching surface.

9. The liquid dispenser as claimed in claim 1, wherein:
the discharge head has a variable internal volume for liquid, which is increased by pushing in an outlet sleeve; and/or
the outlet channel has a shape tapering outward; and/or
the bypass duct surrounds the internal part in an annular manner.

10. The liquid dispenser as claimed in claim 8, wherein:
the switching surface is provided on a side of the discharge head opposite from the base unit for a relative displacement of the internal part and the outlet channel to one another.

11. The liquid dispenser as claimed in claim 1, wherein:
the discharge head is configured to be rotatable about a rotational axis relative to the base unit; and
a mechanism is provided, a rotational movement of the discharge head effecting thereby a relative displacement of the outlet channel relative to the internal part.

12. The liquid dispenser as claimed in claim 11, wherein:
the mechanism comprises a guide element with an angular-dependent spacing from the rotational axis and which is provided on the internal part or the outlet sleeve of the discharge head or on the base unit; and
the mechanism comprises a guide slider which is in engagement with the guide element and which is provided on the base unit or on the internal part or the outlet sleeve of the discharge head.

13. The liquid dispenser as claimed in claim 1, wherein:
the discharge head is provided rotatably on the base unit; and
the discharge head has a mechanism by which a relative position of the internal part is adjustable relative to the outlet channel.

14. The liquid dispenser as claimed in claim 1, wherein:
the internal part has an outer wall portion and a spray component introduced therein.

15. The liquid dispenser as claimed in claim 1, wherein:
the internal part has a spray component introduced therein, wherein the spray component comprises the spray opening and forms at least part of an inner wall of a swirl chamber.

16. The liquid dispenser as claimed in claim 1, wherein:
in the first relative position, the bypass duct is closed so that liquid may only be dispensed through the spray duct; and
in the second relative position, an inlet into the spray duct is closed so that liquid may only be dispensed through the bypass duct.

17. A liquid dispenser comprising:
a base unit with a liquid reservoir for receiving liquid;
a discharge head comprising a housing connected to the base unit; and
a pump device configured to be actuated by a relative translatory movement of the discharge head relative to the base unit and that conveys liquid out of the liquid reservoir into the discharge head or the liquid reservoir is configured as a pressure accumulator and the liquid dispenser has a valve device configured to be actuated by a relative translatory movement of the discharge head relative to the base unit and conveys liquid out of the liquid reservoir into the discharge head;
the discharge head having a liquid outlet through which liquid is discharged from the liquid reservoir out of the discharge head;
the discharge head having a liquid inlet through which liquid is conducted out of the liquid reservoir to the liquid outlet;
the discharge head being configured for selectively discharging liquid either as an atomized spray jet and as a non-atomized liquid stream or individual droplets;
the discharge head including an outlet channel having an inner surface wall and an internal part inside the outlet channel, the internal part having an outer surface facing the inner surface wall of the outlet channel;
the internal part including a spray duct ending at a spray opening on a front face of the internal part;
the internal part and the outlet channel being relatively displaceable so that in a first relative position, a bypass duct is produced between the inner surface wall of the outlet channel and the outer surface of the internal part, and in the first relative position, a first relative position bypass flow resistance of the bypass duct is lower than a first relative position spray duct flow resistance of the spray duct, and the bypass duct and the internal part have a second relative position wherein a second relative position bypass flow resistance of the bypass duct is higher than a second relative position spray duct flow resistance of the spray duct; and
wherein the liquid flowing through the bypass duct bypasses the spray duct and the spray opening; and
wherein the spray opening moves linearly relative to an outlet opening of the outlet channel.

18. The liquid dispenser as claimed in claim 17, wherein:
the internal part and the outlet channel move only linearly relative to each other.

19. The liquid dispenser as claimed in claim 17, wherein:
the internal part and the outlet channel having a closed relative position wherein liquid is prevented from flowing through the bypass duct while simultaneously flowing through the spray duct and out the spray opening.

* * * * *